US00PP18686P3

(12) United States Plant Patent
Meilland

(10) Patent No.: US PP18,686 P3
(45) Date of Patent: Apr. 1, 2008

(54) FLORIBUNDA ROSE PLANT NAMED 'MEIPOTEN'

(50) Latin Name: ***Rosa hybrida*/Floribunda**
Varietal Denomination: Meipoten

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/476,678

(22) Filed: Jun. 29, 2006

(65) Prior Publication Data

US 2008/0005816 P1 Jan. 3, 2008

(51) Int. Cl.
*A01H 5/00* (2006.01)

(52) U.S. Cl. ..... Plt./143

(58) Field of Classification Search ..... Plt./143
See application file for complete search history.

*Primary Examiner*—Kent Bell
*Assistant Examiner*—S. B. McCormick-Ewoldt
(74) *Attorney, Agent, or Firm*—Buchanan Ingersoll & Rooney PC

(57) ABSTRACT

A new and distinct Floribunda rose plant is provided that forms on a continuous basis attractive long-lasting double blossoms which are soft yellow suffused and edged with Neyron Rose coloration. The buds are very elegant in configuration. The growth habit is very vigorous, semi-erect, and well-balanced. The medium green foliage bears a semi-glossy finish. Good tolerance to cryptogamic diseases has been observed. The plant is well suited for growing as attractive ornamentation in parks and gardens.

1 Drawing Sheet

Figure 1:
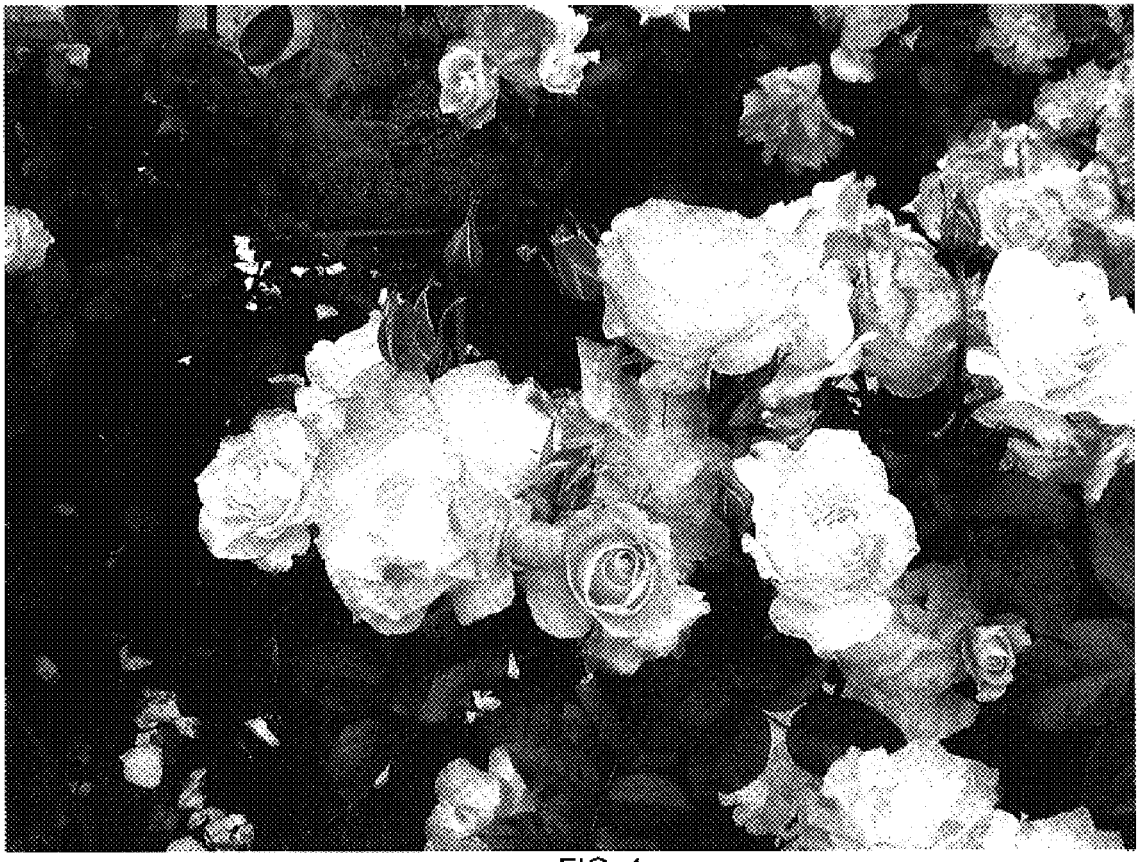

Botanical/commercial classification: *Rosa hybrida*/Floribunda Rose Plant.
Varietal denomination: cv. Meipoten.

SUMMARY OF THE INVENTION

The new *Rosa hybrida* variety of Floribunda rose plant was created by artificial pollination wherein two parents were crossed which previously had been studied in the hope that they would contribute the desired characteristics. The female parent (i.e., the seed parent) of the new variety was in 'BUCbi' variety (U.S. Plant Pat. No. 4,225). The male parent (i.e., the pollen parent) was the product of the cross of the 'Delbara' variety (non-patented in the United States) and the 'Korfalt' variety (non-patented in the United States). The parentage of the new variety can be summarized as follows:

*'BUCbi'×('Delbara'×'Korfalt').*

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms buds having a very elegant configuration, (b) abundantly forms on a continuous basis attractive long-lasting double blossoms which are soft yellow suffused and edged with Neyron Rose coloration, (c) exhibits a very vigorous semi-erect well-balanced bushy growth habit, (d) forms dense medium green semi-glossy foliage, and (e) is well suited for growing as attractive ornamentation in parks and gardens.

Good resistance to disease and to frost has been observed.

The new variety of the present invention can be readily from its ancestors. More specifically, the blossoms of the 'BUCbi' variety are light pink in coloration, the 'Delbara' variety displays a compact growth habit unlike that of the new variety, and the 'Delbara' variety forms yellow blossoms that are red on the reverse of the outer petals.

The new variety of the present invention also can be readily distinguished from other similar Floribunda rose varieties, such as the 'Meibaltaz' (U.S. Plant Pat. No. 8,449) and 'Meimonblan' (U.S. Plant Pat. No. 12,579) varieties. Each forms blossoms having a different coloration. The 'Meibaltaz' variety forms yellow blossoms and the 'Meimonblan' variety forms darker tangerine orange blossoms.

The new variety well meets the needs of the horticultural industry and is particularly well suited for enhancing the appearance of the landscape. Attractive ornamental well-balanced plants are provided.

The new variety has been found to undergo asexual propagation in the South of France and near West Grove, Pa., U.S.A., by a number of routes, including budding, grafting, and cuttage. Asexual propagation by the above-mentioned techniques at such locations has shown that the characteristics of the new variety are stable and are strictly transmissible by such asexual propagation from one generation to another. The new variety asexually reproduces in a true-to-type manner.

The new variety has been named the 'Meipoten' variety.

BRIEF DESCRIPTION OF THE PHOTOGRAPH

The accompanying photograph shows as nearly true as it is reasonably possible to make the same, in a color illustration of this character, a typical specimen the new variety. The rose plant of the new variety was two years of age and was observed during June while budded on *Rosa froebelli* understock and growing outdoors near West Grove, Pa., U.S.A.

FIG. 1 — illustrates typical buds, blossoms in various stages of opening, and foliage of the 'Meipoten' variety.

DETAILED DESCRIPTION

The chart used in the identification of the colors is that of The Royal Horticultural Society (R.H.S. Colour Chart). The description is based on the observation of two year-old plants during June while budded on *Rosa froebelli* understock and growing outdoors near West Grove, Pa., U.S.A. Reference to color in common terms is to be accorded its ordinary dictionary significance.

Class: Floribunda.

Plant:

*Height.*—Approximately 90 to 100 cm on average at the end of the growing season.

*Width.*—Approximately 70 to 80 cm on average at the end of the growing season.

*Habit.*—Bushy and semi-erect.

Branches:

*Color.*—Young stems: light green, Green Groups 143C, and more or less stained with reddish coloration. Adult wood: near Green Group 137B.

*Thorns.*—Size: medium to large, commonly approximately 9.5 to 14 mm (average approximately 12 mm) in length to the base of the stem axis, approximately 2.8 to 3.8 mm (average approximately 3.4 mm) in width perpendicular to the stem axis, and approximately 8.5 to 10 mm (average approximately 9 mm) in vertical height. Quantity: Moderate. Color on young stems: reddish with a greenish tip. Color on adult stems: greenish changing to tan when fully mature.

Leaves:

*Stipules.*—Adnate, pectinate, wide and linear.

*Petioles.*—Upper surface: primarily Yellow-Green Group 144A with some lightening to near Yellow-Green Group 144B with glandular edges, and possibly with some red pigmentation near and through Greyed-Purple Group 185A, 187A, 187B, and 187C. Under surface: Yellow-Green Group 144B with some darkening to near Yellow-Green Group 144A with a few prickles mixed with glandular acicules.

*Leaflets.*—Number: 3, 5, and sometimes 7. Shape: spear-like. Size: terminal leaflets commonly are approximately 7 cm in length on average and approximately 3.5 to 4 cm in width on average Serration: single and regular. Texture: leathery. General appearance: dense, medium green, and semi-glossy. Color (young foliage): upper surface: commonly between Greyed-Purple Group 183B and Greyed-Purple Group 187C. under surface: commonly between Greyed-Purple Group 183B and Greyed-Purple Group 187C. Color (adult foliage): upper surface: medium green, Yellow-Green Group 147B. Under surface: light green, Yellow-Green Group 147C.

Inflorescence:

*Number of flowers.*—Commonly in clusters of 1 to 7 flowers per stem.

*Peduncle.*—Rather straight, rigid, near Yellow-Green Group 144A and more or less suffused with near Greyed-Purple Group 183B and Greyed-Purple Group 187C, bears numerous pediculate glands, and the length commonly is approximately 6 cm on average.

*Sepals.*—Upper surface: tomentose, near Yellow-Green Group 144B at the base, and more or less suffused with Greyed-Purple Group 183C at the tip. Under surface: light green, more or less stained with reddish coloration. Bear glandular edges that are slightly appendulated.

*Buds.*—Shape: generally oval with an elegant shape. Size: Small. Length: approximately 2.5 cm on average. Color upper surface: upon opening light Mimosa Yellow, Yellow Group 8D, and lightly edged and suffused with Venetian Pink, Red Group 49B. Color under surface: upon opening light Mimosa Yellow, Yellow Group 8D. Spot at base: none observed.

*Flower.*—Shape: double and generally flat-shaped. Diameter: approximately 9 to 10 cm on average when fully open. Color (when opening begins): upper surface: light Mimosa Yellow, Yellow Group 8D, and lightly suffused and edged with Venetian Pink, Red Group 49B. Under surface: light yellow, Yellow-White Group 158C. Color (when blooming): upper surface: light yellow, Yellow Group 8C, and widely suffused with Neyron Rose, Red Group 55B. Under surface: pale Chrome Yellow, Yellow-White Group 158D. Color (at end of opening): upper surface: light yellow, Yellow Group 8C, and very widely suffused and edged with Neyron Rose, Red Group 55B. Under surface: pale Chrome Yellow, Yellow-White Group 158D. Petal number: approximately 24 to 25 on average under normal growing conditions. Petal arrangement: imbricated. Petal configuration: reflexed tip and an obtuse base. Petal shape: generally oval with a corrugated tip. Petal size: approximately 3.5 cm in length on average, and approximately 3 cm in width on average. Petal texture: rather firm and consistent. Petal margin: wavy and somewhat reflexed (as illustrated). Petaloids: none observed. Stamen: approximately 88 to 94 on average. Anthers: near Yellow Group 13C and Yellow-Orange Group 16A and typical in form. Filaments: commonly of irregular heights, free-standing, and near Yellow Group 13C. Pistils: approximately 47 to 52 on average. Styles: tomentose at the base, near Yellow Group 8D and at the tip Yellow Group 8A more or less twisted in form, and commonly of irregular heights. Stigmas: located at substantially the same level as the anthers, typical in form, and near Yellow Group 8D and Yellow Group 9D. Fragrance: none. Lasting quality: long. Petal drop: good, the petals commonly detach cleanly before drying. Receptacle: smooth, near Yellow-Green Group 144A, approximately 4.2 to 8.2 cm (average approximately 5.7 cm) in length, and in longitudinal section in the shape of narrow funnel.

Development:

*Vegetation.*—Very vigorous.

*Blooming.*—Very floriferous with continuous blooming throughout the season.

*Tolerance to diseases.*—Good tolerance to cryptogamic diseases is exhibited.

*Tolerance to frost.*—Very good.

*Aptitude to bear fruit.*—Good.

I claim:

1. A new and distinct Floribunda Rose plant having the following combination of characteristics:

(a) forms buds having a very elegant configuration, (b) abundantly forms on a continuous basis long-lasting double blossoms which are soft yellow suffused and edged with Neyron Rose coloration, (c) exhibits a very vigorous semi-erect well-balanced bushy growth habit, (d) forms dense medium green semi-glossy foliage, and (e) is well suited for growing as attractive ornamentation in parks and gardens; substantially as illustrated and described.

* * * * *